(12) United States Patent
Langlotz

(10) Patent No.: US 6,366,683 B1
(45) Date of Patent: Apr. 2, 2002

(54) APPARATUS AND METHOD FOR RECORDING IMAGE ANALYSIS INFORMATION

(76) Inventor: Curtis P. Langlotz, 5 Biddle Way, Mt. Laurel, NJ (US) 08054

( * ) Notice: Subject to any disclaimer, the term of this patent is extended or adjusted under 35 U.S.C. 154(b) by 0 days.

(21) Appl. No.: 09/268,872

(22) Filed: Mar. 16, 1999

(51) Int. Cl.$^7$ ................................................ G06K 9/00
(52) U.S. Cl. ...................................... 382/128; 128/922
(58) Field of Search ................................. 382/128, 131, 382/129, 130, 132; 707/500

(56) References Cited

U.S. PATENT DOCUMENTS

| | | | | |
|---|---|---|---|---|
| 5,115,501 A | * | 5/1992 | Kerr ............................... | 707/9 |
| 5,148,366 A | * | 9/1992 | Buchanan et al. .............. | 707/5 |
| 5,267,155 A | * | 11/1993 | Buchanan et al. .............. | 707/5 |
| 5,506,984 A | * | 4/1996 | Miller ............................ | 707/10 |
| 5,581,460 A | * | 12/1996 | Kotake et al. .................. | 705/3 |
| 5,666,400 A | * | 9/1997 | McAllister et al. ............ | 379/88 |
| 5,715,449 A | * | 2/1998 | Peters, Jr. et al. .............. | 707/1 |

OTHER PUBLICATIONS

Bell D, Greenes R. Evaluation of UtraSTAR: Performance of a collaborative structured data entry system *J Am Med Informatics Assoc* 1994;Symposium Supplement:216–222.*

Bell D, Pattison–Gordon E, Greenes R. Experiments in concept modeling for radiographic image reports. *J Am Med Informatics Assoc* 1994;1:249–262.*

Campbell K, Wieckert K, Fagan L, Musen M. A computer-based tool for generation of progress notes. *J Am Med Informatics Assoc* 1993;Synposium Supplement:284–288.*

Dockray K Solo practice management: Value of a computerized reporting system *AJR American Journal of Roentgenology* 1994;162:1439–1441.*

Friedman C, Cimino J, Johnson S. A schema for representing medical language applied to clinical radiology. *J Am Med Informatics Assoc* 1994;1:233–248.*

Hundt W, Adelhard K, Hundt C, Nissen–Meyer S, Kohz P, Fink U, Reiser M. A computer–based reporting system in radiology of the chest. *European Radiology* 1998;8:1002–1008.*

Kahn C, Wang K, Bell D. Structured entry of radiology reports using world–wide web technology. *Radiographics* 1996;16:683–691.*

Pendergrass H, Greenes R, Barnett G, Pouters I, Pappalardo A, Marble C. An on–line computer facility for systematized input of radiology reports. *Radiology* 1969;92:709–713.*

Poon A, Fagan L. PEN–Ivory: The design and evaluation of a pen–based computer system for structured data entry. *J Am Med Informatics Assoc* 1994;(Symposium Supplement):447–451.*

Puerta A, Eisenstein I. Towards a general computational framework for model–based interface development systems. In Proceedings of the International Conference on Intelligent User Interface Design. Los Angeles, CA, 1999:(forthcoming).*

* cited by examiner

*Primary Examiner*—Joseph Mancuso
*Assistant Examiner*—Abolfazl Tabatabai
(74) *Attorney, Agent, or Firm*—Bennet K. Langlotz PC; Bennett K. Langlotz

(57) ABSTRACT

A system and method of generating an image analysis report relating to an image of a subject. The method includes querying a user for an image description providing locational information regarding the image, querying the user for a physical description providing locational information regarding the subject, and querying the user for a finding description providing selected characteristics of the image. A description set including the user's responses to the queries is stored and processed to generate the report. Any of the querying steps may include providing the user with a limited set of entry options, and some of the entry may be by selecting a location on a graphical map. A second description set relating to a different image of the same or a different subject may also be entered, and the user may be queried for information relating to a causal link between the description sets. A user may be queried for a confidence level of any observation or conclusion.

20 Claims, 2 Drawing Sheets

APPARATUS AND METHOD FOR RECORDING IMAGE ANALYSIS INFORMATION

FIELD OF THE INVENTION

This invention relates to data entry systems, and more particularly to systems for generating reports of image analyses.

BACKGROUND AND SUMMARY OF THE INVENTION

The process of medical image interpretation has been fundamentally unchanged for decades. The radiologist or other medical imaging professional sits or stands while visually examining images displayed on a stationary light box or a film alternator (a motor driven machine that allows the display of 50 or more sets of filmed images). While studying and interpreting the images, the radiologist typically dictates findings and conclusions from the examination into a recording device. Smaller practices often use a tape recorder and an in-house medical typist; larger practices may use telephone lines to transmit dictations to a contracted off-site transcription company. After transcription, the report is made available, either on paper or in electronic form, to the interpreting radiologist for editing and subsequent signature. This signed report serves as the primary work product of radiologists and other imaging specialists.

Although medical image interpretation comprises a large part of many medical specialties, including cardiology, pathology, gastroenterology, and surgery, radiology is used to herein illustrate the prototypical medical interpretation process. The practice of radiology is the most image-intensive medical specialty—most radiology practices generate income almost exclusively from the production and interpretation of medical images.

Referring physicians who request that the radiologist perform an interpretation of the image, health care payors, and courts view the imaging report as an official document that is the final product of an imaging examination. Because the dictated report is the formal means of communication between the radiologist and the referring physician and because its findings and conclusions are often the basis for vital medical treatment decisions, its accuracy and timeliness are essential. Many health care organizations, including the Joint Commission on Accreditation of Hospital Organizations (JCAHO), require that a final written report of each imaging examination be available in the patient's permanent record in a timely fashion (usually 24 hours). Some health care payors have considered implementing this requirement as a condition of reimbursement for professional imaging services.

Many radiology practices routinely fail to achieve this benchmark for report finalization. As a result, shortening the report dictation-transcription-signature cycle has been the subject of substantial concern and study. Despite this heightened level of concern, report finalization times have been resistant to change.

There are several important limitations of conventional reporting and transcription. Transcription services are costly, contributing substantially to the overhead of radiology practice revenues. The purchase and maintenance of recording hardware, electronic communication lines, modems, and information systems components add to this cost.

Transcribed preliminary reports often are not available in a timely fashion. Recorded dictations are subject to accidental erasure or loss. Electronic or phone-based systems sometimes lose data, or capture dictations with poor data integrity, resulting in inaccurate or unreported imaging examinations. These problems delay the final report, thereby frustrating the referring physician, delaying or preventing reimbursement for the examination, and degrading practice efficiency. Some phone-based systems allow a referring physician to hear an unedited preliminary dictation created by a trainee radiologist. But these services are used infrequently because the report is not final, and must be accessed in linear fashion, requiring the referring physician to listen to the entire report from the beginning, with limited ability to rewind or fast-forward.

Transcriptionists have a significant error rate, with a significant fraction of these errors being substantive, such as errors of missing or incorrect information that would have led to unnecessary treatment or testing, or that could have caused risk of complications or morbidity for the patient.

Report signature causes additional delays. Even when preliminary (unedited) reports are available on a radiology information system, they are often of limited utility to the referring physician. Transcription errors are frequent. At teaching institutions, these preliminary reports are usually dictated by trainees, and have not yet been reviewed, edited, and signed by the senior physician legally responsible for the report.

The text report often does not meet the needs of referring physicians. Reports sometimes do not in the opinion of referring physicians address the clinical question, or may be confusing. A multitude of different terms may be used to describe a single common abnormal finding leading to further confusion.

The text report is frequently vague, incomplete, or inaccurate. Although the American College of Radiology has developed standards for the diagnostic radiology report and encourages "precise anatomic and radiological terminology to describe the findings accurately," no adequate terminology or lexicon has been developed to capture the semantic content of a diagnostic imaging report. For example, one study found that three existing lexicons, the Unified Medical Language System (UMLS) Meta-thesaurus, the Systematic Nomenclature for Medicine (SNOMED), and the American College of Radiology (ACR) codes, contained only 14%, 23%, and 19%, respectively, of the terms needed to capture the meaning of a specific type of imaging report.

A text report has minimal utility for subsequent practice management and data mining. Even in the best of circumstances, when the transcribed and signed report is available on a radiology information system, only an unstructured text format is available. Text-based searches of those systems can be time consuming, and have low accuracy in retrieving a desired subset of reports. Because the semantic content is not stored or indexed in a semantically-coherent fashion, expensive and inaccurate post-processing or re-coding of the data is required if additional analyses are required. The lack of structure and consistency of a free-form dictated or written report also leads to high transmission and storage costs, and the inconsistencies may lead to vague and unclear reports.

Computer software systems have been created to provide a substitute for dictation, but these have been found to suffer limitations. For instance, U.S. Pat. No. 5,267,155 to Buchanan et at describes a system in which a document template includes "boiler plate" text, with "holes" to be filled in by a physician based on an examination. While useful for certain simple needs, this is insufficiently flexible and expressive to meet the standards for certain more complex radiology reports, for instance, as well as numerous other image analysis reports. These more complex reports may involve multiple images with multiple findings, arbitrary ordering of sentences, as well as complex causal linkages and degrees of belief or confidence, which existing systems can not convey. The multitude of possible terms and findings for such applications would require an intractably large number of templates, with locating an appropriate template taking far more resources than simply generating a manual report.

The embodiment disclosed herein overcomes these disadvantages by providing a system and method of generating an image analysis report relating to an image of a subject. The method includes querying a user for an image description providing locational information regarding the image, querying the user for a physical description providing locational information regarding the subject, and querying the user for a finding description providing selected characteristics of the image. A description set including the user's responses to the queries is stored and processed to generate the report. Any of the querying steps may include providing the user with a limited set of entry options, and some of the entry may be by selecting a location on a graphical map. A second description set relating to a different image of the same or a different subject may also be entered, and the user may be queried for information relating to a degree of belief in a description set and/or relating to a causal link between the description sets.

DEFINITIONS

Figure 1:
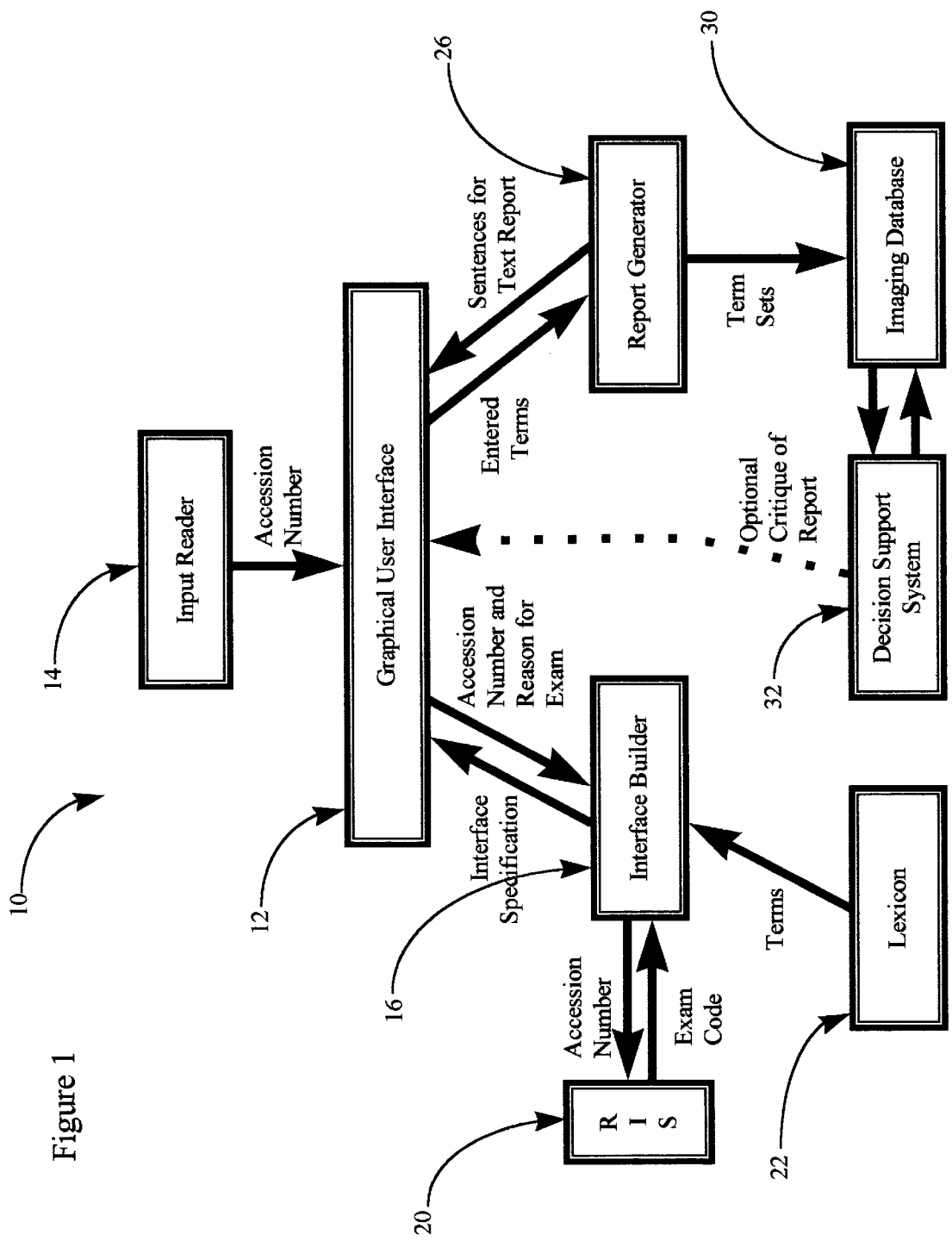
FIG. 1 is a block diagram of a system according to the preferred embodiment of the invention.

The preferred embodiment is discussed in terms of the following defined terms, the definitions of which are offered for clarity of a single embodiment and are not intended to be limiting of all possible contemplated embodiments.

Image: The visual representation of a physical object made by means of detecting energy of one or more wavelengths reflected from, projected through, refracted by, or otherwise transmitted or modified by a physical object.

Display Medium: The medium or device on which the image is displayed (e.g., conventional emulsion-based film, computer workstation display, hologram, etc.)

Imaging Technique: The means by which an image is created, including (1) the geometric relationship of energy beam, physical object, and energy detection system, (2) the positioning or configuration of the physical object, (3) the type of energy used and the energy detection system used, and (4) the display medium.

Term: A character string signifying a particular element of a description set (e.g., X-ray, film, opacity).

Lexicon: A set of one or more terms.

Imaging Lexicon: The set of terms describing a location with respect to the display medium and imaging technique, including the individual elements of the image itself (e.g., pixels, voxels) and their location on the display medium (e.g., top of the chest X-ray film, the corner of the 15th T1-weighted MRI image).

Physical Lexicon: The set of terms describing a physical location with reference to the actual physical structure being imaged (e.g., the human body, the heart, the observed tumor, the surface of the earth, the hill, the microbe, the cracked pipe).

Finding Lexicon: The set of terms describing features of an image, or inferences about the physical domain made from features of an image, that may be included in the image description (e.g., lucency, opacity, high signal, red area).

Modifier Lexicon: The set of terms that modify single terms from the imaging, physical, and findings lexicons, in order to restrict further the location of a term in the imaging, physical, or findings lexicons (e.g., left, anterior, proximal), to further specify the number, size, morphology, uniformity, severity, or other characteristic of a term (e.g., multiple, large, flat, homogeneous, hazy, mobile, chronic).

Confidence Level: An integer from a pre-defined scale used to represent the degree of belief or likelihood that a term or terms accurately applies to the image.

Imaging Description: A set of terms from the Imaging Lexicon, together with a set of terms from the Modifier Lexicon and a Confidence Level. (Each may be the empty set.)

Physical Description: A set of terms from the Physical Lexicon, together with a set of terms from the Modifier Lexicon and a Confidence Level (Each may be the empty set.)

Finding Description: A set of terms from the Findings Lexicon, together with a set of terms from the Modifier Lexicon and a Confidence Level. (Each may be the empty set.)

Description Set: A triplet composed of an Imaging Description, a Physical Description, and a Finding Description. Detailed further below.

Relation Lexicon: The set of terms that signify logical relationships among two or more Description Sets (e.g., in/near, above/below, and/or, causes, represents, is associated with, otherwise/except, if/then).

Relation Set: A term from the Relation Lexicon, together with references to the Sentences (defined below) to which the term applies and a Confidence Level.

Sentence: A Description Set or a Relation Set.

Imaging Report: A set of Sentences that describe the important findings in an image.

DETAILED DESCRIPTION OF A PREFERRED EMBODIMENT

FIG. 1 is a block diagram of a software architecture 10 of the preferred embodiment invention. The software is stored in a computer. Boxes represent computational components, and arrows represent the flow of data, information, or knowledge. Although the system is discussed in terms of software, it may be embodied in any form capable of processing and transmitting information. The software operates to enable a radiologist or any image analyst to call up from a database basic identifying information about an image, and to efficiently enter an analysis of the image. The entered analysis is constrained by the lexicons above and to a standardized format suitable for storage in a database or for other analysis, and is converted to a report including graphic images and normal grammatical text that is as easily interpreted by a referring physician.

The system includes a graphical user interface (GUI) 12 that is connected to an input reader 14 that receives and decodes input from any of several input devices. In the preferred embodiment, the input device is a bar code reader, although an audio microphone, mouse, or keyboard may be used. In any case, the input reader converts the signal of the input device to a numerical accession number.

An interface builder block 16 is connected to the GUI and an external database interface 20 (such as a radiology information system or RIS normally used to enable radiologists to manage many aspects of their practices) connects to the interface builder. An lexicon storage block 22 also connects to the interface builder. The RIS 20 contains an external database of records labeled by unique accession numbers, each of which identifies an individual image or set of images for which the report will be generated. In response to receiving an accession number from the GUI, the interface builder block 16 transmits the accession number to the RIS, which returns to the interface builder an image code. An image code is a standardized code indicating the nature of a radiological image, such as is commonly used by a referring physician to instruct radiologists and/or radiological technicians what image is required. The image code conveys information about what part(s) of the body is to be imaged, from what direction(s), the patient's orientation(s) (e.g. erect, prone, supine), and the imaging technology(ies).

Along with the image code, the interface builder receives from the RIS 20 other information, including patient name, medical history, and any other information normally provided to a radiologist by a referring physician. Based on the image code and other information received from the RIS, the interface builder constructs a suitable interface specification that has input prompts that pertain to the image, including sets of terms drawn from the lexicon block 22. The lexicon block is essentially a stored dictionary of terms from the imaging lexicon, physical lexicon, finding lexicon, and relation lexicon defined above. These terms are the entire vocabulary from which the radiologists may draw in generating an analysis report. The interface specification is transmitted to the GUI 12, which converts the interface specification into a displayable format.

Figure 2:
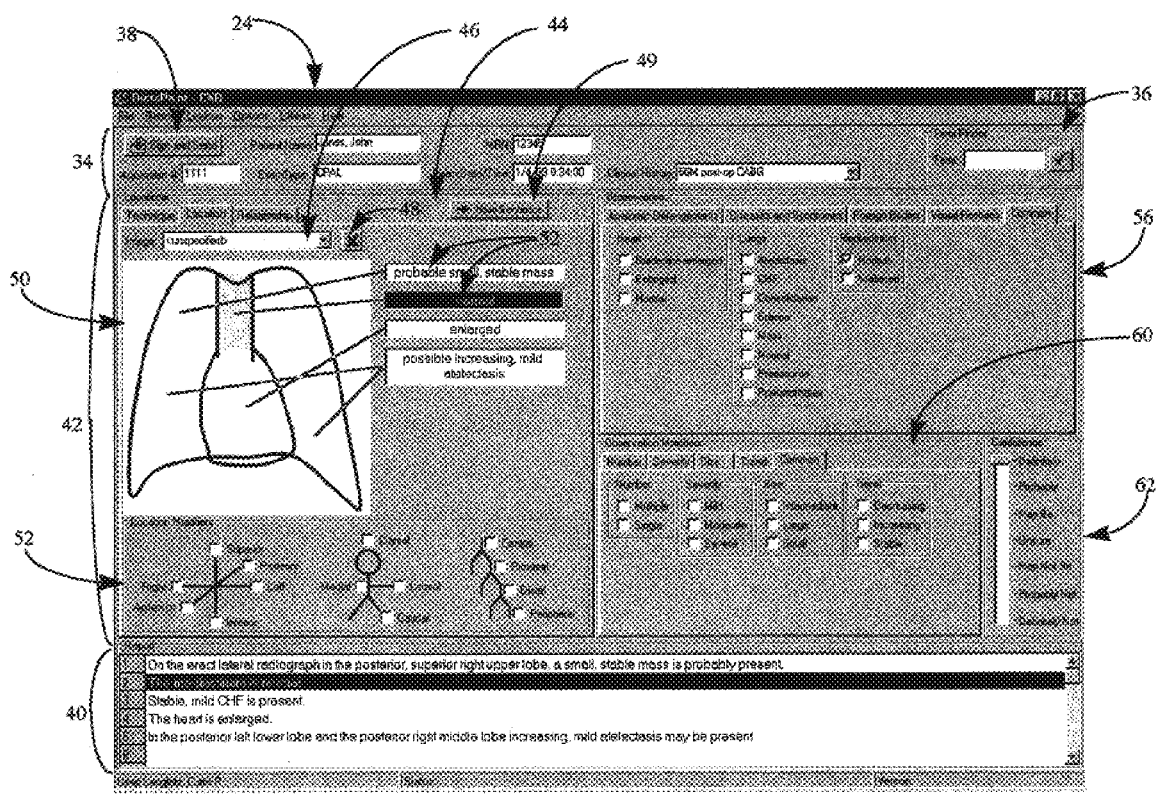
FIG. 2 is a display screen generated by the embodiment of FIG. 1.

The radiologist or other user views an electronic display of the interface screen 24 as shown in FIG. 2, and input information indicating findings or conclusions about the medical image being analyzed. These are entered by way of a mouse or other input device that may use a cursor to select appropriate locations, words, check boxes and the like displayed on the screen. These are selected arbitrarily for each case based on the user's preferences, and/or based on what is intuitively appropriate to the user for the particular circumstances. Alternatively, a speech recognition input method not using a cursor may be used. The screen may change during the input process to provide additional selection options, to offer a narrower and more specific range of input selections based upon the initial inputs.

Returning to FIG. 1, a report generator 26 is connected to the GUI 12 to receive the terms selected by the user from the interface. The report generator converts the selected terms into grammatical sentences, and returns the sentences to the GUI for display to the user. In addition to creating a text report for human readers, the report generator also generates a coded report containing the same information in a format that is readily stored, catalogued, and compared with other reports. This coded report is organized as description sets and relation sets, and is transmitted to an imaging database 30 connected to the report generator. The database stores the reports, where they may later be accessed for reconversion to text format, or for further analysis. A decision support system 32 is connected to the imaging database, and operates optionally to compare the user's report entry with other previously stored reports, and to generate a report critique to the user immediately upon entry. Such critique may indicate if the user's report departs unusually from normal entries, based on the user's or other users' prior report history, or based on commonly accepted imaging practices.

FIG. 2 shows a typical display screen 24, which is divided into several regions. Below the standard title and menu bars, a exam information portion 34 displays to the user information pertaining to a single patient examination, which may include more than one image. The information includes accession number, patient name, exam type, MRN (medical record number, a unique identifier associated with the patient), exam date and time, and a synopsis of the patient's clinical history. This information may be displayed as provided from the RIS 20 based on the accession number, or some fields may be filled manually by the user. At the top left of the exam information portion 34, a "sign and send" button 38 allows the user to indicate that the report is complete and should be prepared for signature prior to transmission to the referring physician. To the right of the information portion 34, a search portion 36 includes a term finder utility that allows the user to enter a term he/she desires to use in a report. This is normally not needed, but is provided to guide a user toward appropriate screens that display options including the searched term.

At the bottom of the screen, a text display portion 40 has multiple lines, each for displaying a grammatical sentence corresponding to information entered by the user, so that he/she may read instantaneously the text sentences corresponding to the information entered, to ensure that the report accurately contains the intended information prior to transmission back to the referring physician.

Between the information portion 34 and the text portion 40, the majority of the screen is filled by an input portion 42. The left half of the input region is used for entry of location information, and the right half is used for entry of observations or finding information. A location box 44 includes tab card features labeled "technique", "location", and "relationship". Not normally selected, the "technique" tab card allows the user to enter or edit exam information relating to the imaging technique, if the exam information received form the RIS is incomplete. Normally, as shown, the "location" tab is selected to display the location card. An upper text window 46 allows the user to select an image from a multiple image exam for comment. A delete button 48 allows the user to delete a previously selected image term, such as when the image term was incorrectly selected, or when the observation need not be limited to the particular image. The "relationship" tab allows selection of existing text sentences and specification of relationships between the selected sentences. A "new sentence" button 49 allows the user to indicate that the current sentence is complete, and that he/she wishes to enter an additional sentence.

An image map 50 displays a simplified graphic representation of the anatomic region in the image being analyzed. The image is typically either in the form of a conventional emulsion-based film positioned nearby, or in electronic form on an adjacent high resolution monitor. Each of the multitude of image maps available for display is divided into subregions, each corresponding to a definable anatomical feature, region or part. When such a subregion is selected, the name of the anatomic region is displayed in the text portion 40, and an observation label box 52 opens to the right of the image map, with a line extending from the observation box to the selected subregion.

To indicate a more specific location in the subregion, a location modifier box 54 below the image map provides check boxes arranged spatially to allow intuitive entry of location modifier terms. When a subregion is selected, the associated observation label box 52 is highlighted, and the terms checked apply only to that subregion, and are included in the line of the text portion corresponding to the observation relating to that subregion.

At any time, the user can select the findings or observations relating to that subregion in the right portion of the input portion 42. An observation box 56 includes several tab cards, with a card labeled "common" initially displayed. This includes a limited set of commonly used terms in several different categories. Both the categories and the terms are selected by the interface builder to pertain to the image type, exam type, and/or the anatomical region. The categories are specific anatomical regions represented in the image map, with a set of finding terms appropriate to each anatomical region representing the most common findings associated with each region. Other tabs allow entry of detail relating to more specific findings in different categories such as anatomic derangements, visual features (i.e. opacity, lucency, attenuation, hypoechoic region, displayed color), diseases and syndromes, and foreign bodies, for example.

An observation modifier box 60 and a confidence box 62 are positioned below the observation box 56. The observation modifier box 60 allows the selected observation term or terms to be modified to provide needed specificity. A set of tab cards is provided, with a tab labeled "common" selected by default. The common tab includes limited modifier term selection within the categories of number, size, severity, and trend, for example. Where more specific terms are needed in any of these categories, a tab card corresponding to the category is selected to display a card having many more terms within the category. For instance, while only "multiple" and "single" terms for number are allowed in the "common" card, selecting the number card may allow the choice of terms including various numerals, and any other words indicating quantity.

The confidence box 62 provides a scale labeled with several confidence terms indicating degrees of probability or confidence ranging from certainty in the negative to certainty in the positive, with uncertainty in the middle. For each observation, the user is permitted to select a confidence level, ensuring that the referring physician is provided with this important information. If none is selected, the highest confidence level (i.e. "definitely") is selected by default.

System Operation

In normal operation, the user/radiologist/image analyst enters the accession number, such as by reading a bar code attached to a patient file folder carrying a set of image films. Alternatively, the system may accept the accession number directly from the RIS. If the accession number is from a bar code, the number is validated by the RIS, and a image code is returned. The user then approves or enters the reason for exam from a selection of alternatives from a menu based on ICD9 codes (which is a diagnostic code used for billing and other purposes). The ICD9 code, image codes, and any other diagnostic or patient information are sent to the interface builder, which returns an interface specification for a particular imaging modality and anatomic region. The GUI then displays an appropriate limited set of selectable imaging terms.

The user then selects findings and conclusions using a pointing device, although alternative methods such as speech recognition may be employed. The input process is discussed in detail below. The selections are then transmitted to the report generator, either after all input, or preferably continuously during input to enable the generated text to be returned during the input process for editing during the input process. The generated text is displayed for editing and the signature of the user. When the report is finalized, it is submitted to the RIS. In parallel, the report generator sends symbolic expressions representing the findings and conclusions to the database, which serves as an imaging report knowledge base. The decision support system reaches its own conclusions from the findings. If a potential conflict is found between the system's conclusions and those of the user, a critique of the report is offered.

The details of input by the user proceed as follows. The display screen 24 is displayed on the user's computer work station, after the exam information is retrieved. In the case of electronic imaging, the images themselves may also be received at this time and displayed on an adjacent monitor.

The system selects an image map 50 appropriate to the first of the images. After observing the image and making a first finding, the user normally enters the finding by selecting the subregion of the image map corresponding to the image location of the finding or to the anatomical location of the finding. Then, user normally enters any location modifiers, observation terms, observation modifiers, location modifiers, and a confidence term, in any order. While the observation or finding term may normally be selected before the observation modifiers, the user is unconstrained in the sequence of input. Text display occurs as information is entered. Upon selection of an image map subregion, the image identifier is displayed on the first line of the text region. As selections are made, the observation term, confidence term and all modifiers are included in the displayed sentence.

Additional findings in the image are entered by the user pressing a "new sentence" button 49 that concludes the current sentence, which is saved and displayed as noted below. The "new sentence" button also clears the current selections in the "locations" and "observations" boxes for entry of a new sentence. For the new sentence, the user normally selects an anatomical subregion on the image map, and proceeds as above to enter information about that finding. A new text line is generated in the text portion 40 for each new sentence.

When the user desires to indicate a causal or other relationship between sentences corresponding to findings, he/she selects the Relationship tab, and chooses a term from a selection of relation terms drawn from the relation lexicon. Then, the user chooses from the sentences already entered, indicating to which sentence the relation term applies.

A Medical Example

The Description Set is intended to represent the three key parts of an observation about an imaging examination:

the location of the finding on the imaging study as it is displayed (e.g., "on the corner of the lateral view", "on the post-contrast images", or "on image 12 of series 3");

the anatomic location of the finding (e.g., "in the apex of the left lung", "in a branch of the left pulmonary artery", or "in the anterior mediastinum"); and the finding itself (e.g. "moderate congestive heart failure", "a single large mass", "a nodular opacity", or "an ill-defined consolidation").

Each of the above three components of a Description Set is composed of a primary term and a set of secondary modifier terms. Thus, the phrase "a single large mass" is specified by the primary term "mass" and the modifier terms "single" and "large." The phrase "in the apex of the left lung" is represented by the term "lung" and the modifier terms "apex" and "eft." The phrase "on the corner of the lateral view" is specified by the term denoting "lateral view" with the modifier term "corner." Thus, the following Sentence:

[SENTENCE:
  SENTENCE NUMBER: 1
  [DESCRIPTION SET:
    [IMAGING DESCRIPTION:
      IMAGING TERMS: {LATERAL VIEW}
      MODIFIERS: {CORNER}
      CONFIDENCE: 7]

```
[PHYSICAL DESCRIPTION:
    PHYSICAL TERMS: {LUNG}
    MODIFIERS: {APEX, LEFT}
    CONFIDENCE: 7]
[FINDING DESCRIPTION:
    FINDING TERMS: {MASS}
    MODIFIERS: {SINGLE, LARGE}
    CONFIDENCE: 6]]]
```
corresponds to the following text sentence:

"On the corner of the lateral view, in the apex of the left lung, there is probably a single, large mass."

Likewise a second description set:
```
[SENTENCE:
    SENTENCE NUMBER: 2
    [DESCRIPTION SET:
        [IMAGING DESCRIPTION:
            IMAGING TERMS: {PA VIEW}
            MODIFIERS: { }
            CONFIDENCE: 7]
        [PHYSICAL DESCRIPTION:
            PHYSICAL TERMS: {LUNG}
            MODIFIERS: {LATERAL, APEX, LEFT}
            CONFIDENCE: 7]
        [FINDING DESCRIPTION:
            FINDING TERMS: {CONSOLIDATION}
            MODIFIERS: {SMALL, DENSE}
            CONFIDENCE: 5]]]
```
corresponds to the following text description:

"On the posteroanterior view, in the lateral apex of the left lung, there may be small, dense consolidation."

Finally, the following Sentence:
```
[SENTENCE:
    SENTENCE NUMBER: 3
    [RELATION SET:
        RELATION TERM: CAUSES
        FIRST REFERENT SENTENCE NUMBER: 1
        SECOND REFERENT SENTENCE NUMBER: 2
        CONFIDENCE: 6]]
```
corresponds to the following text description:

"The mass probably causes the consolidation."

These three sentences, taken together, comprise a brief Imaging Report:

"On the corner of the lateral view, in the apex of the left lung, there is probably a single, large mass. On the posteroanterior view, in the lateral apex of the left lung, there may be small, dense consolidation. The mass probably causes the consolidation"

While the disclosure is made in terms of a preferred embodiment, the invention is not intended to be so limited.

What is claimed is:

1. A method of generating an image analysis report relating to an image of a subject, the method comprising:
   querying a user for an image description providing locational information regarding the image;
   querying the user for a physical description providing locational information regarding the subject;
   querying the user for a finding description providing selected characteristics of the image;
   storing a description set including the user's responses to the queries; and
   processing the description set to generate the report.

2. The method of claim 1 wherein at least one of the steps of querying the user includes the step of providing the user a first limited set of input options.

3. The method of claim 2 including providing the user with a second limited set of input options selected from a group of input option sets, the second set being selected based on a recorded selection by the user from among the first set.

4. The method of claim 1 wherein at least one of the steps of querying the user includes querying the user for a confidence level regarding the description that is the subject of the description associated with the at least one step of querying.

5. The method of claim 1 wherein at least one of the steps of querying the user includes displaying a graphical map, and includes recording a location on the map selected by the user.

6. The method of claim 5 wherein the map is a representation of at least one of the image and the subject.

7. The method of claim 1 wherein the image is a medical image and the subject is a patient.

8. The method of claim 1 wherein the step of processing includes generating a text sentence.

9. The method of claim 1 including querying the user for a second image description of a second image, a second physical description of the second subject, and a second finding description, and storing the user's responses to the queries in the form of a second description set.

10. The method of claim 9 including querying the user for a relation description of a relationship between the description set and the second description set.

11. A method of generating an image analysis report relating to an image, the method comprising:
    presenting a user with a first limited set of entry options relating to the image and a second limited set of entry options relating to the image;
    storing a first entry selected by the user from one of the first and second sets;
    based on the first entry, presenting the user with the entry options associated with the other of the entry option sets;
    storing a second entry selected by the user from the other of the entry option sets; and
    processing the first entry and the second entry to generate a report.

12. The method of claim 11 wherein the image is a medical image, and including receiving an image request from a referring physician, and including transmitting the report to the referring physician.

13. The method of claim 11 wherein the first set of entry options signifies alternative anatomical locations, and wherein the second set of entry options signifies observations related to a selected one of the anatomical locations.

14. The method of claim 11 wherein presenting the user with a first limited set of entry options includes displaying an anatomical map.

15. The method of claim 11 wherein the steps of presenting and storing include querying the user for characteristics of the image, for a physical description of the subject of the image, and for a finding regarding the image.

16. The method of claim 11 including querying the user for a confidence level related to at least one of the first and second entries.

17. The method of claim 11 including presenting options and storing entries by the user relating to a second image, and querying the user for a relation description of a relationship between the entries relating to the first image and those of the second image.

18. A computer-based image analysis report-generating system comprising:
    input means for querying a user for an image description providing locational information regarding the image, for querying the user for a physical description providing locational information regarding the subject, and for querying the user for a finding description providing selected characteristics of the image;

storage means for storing a description set including the user's responses to the queries; and processing means for processing the description set to generate the report.

19. The system of claim 18 wherein the input means includes means for providing the user a first limited set of input options.

20. The system of claim 18 wherein the input means includes means for querying the user for a confidence level regarding at least a portion of the description set.

* * * * *